Figure 1B:
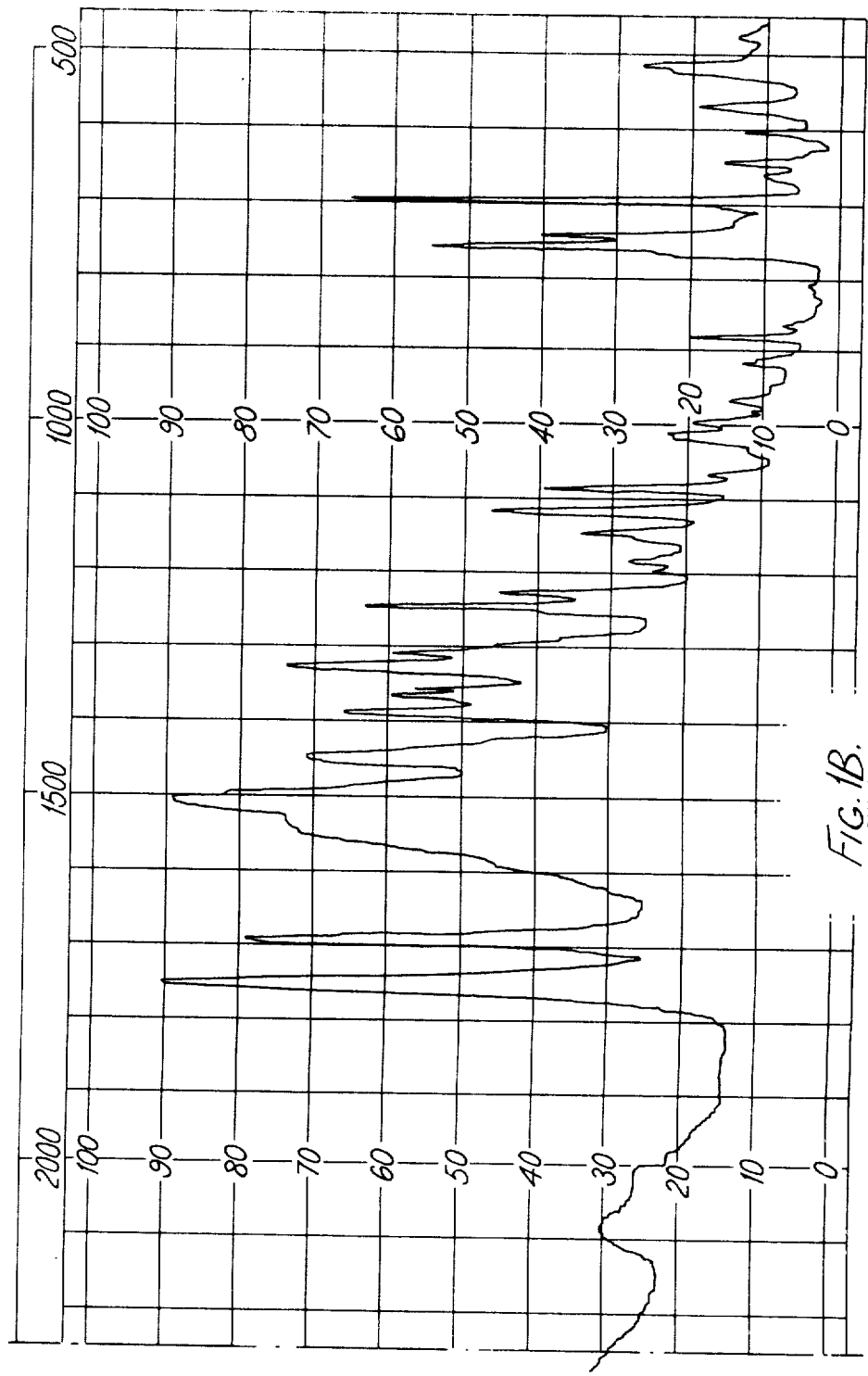

United States Patent [19]

Parker et al.

[11] 3,933,796

[45] Jan. 20, 1976

[54] ANTIBIOTICS

[75] Inventors: Arthur Coates Parker, Uxbridge; Susan Elizabeth Staniforth, London, both of England

[73] Assignee: Glaxo Laboratories Limited, Greenford, England

[22] Filed: June 11, 1974

[21] Appl. No.: 478,309

[30] Foreign Application Priority Data

June 15, 1973 United Kingdom............... 28690/73

[52] U.S. Cl............................... 260/239.1; 424/271
[51] Int. Cl.$^2$....................................... C07D 499/68
[58] Field of Search.................................. 260/239.1

[56] References Cited
UNITED STATES PATENTS

| | | | |
|---|---|---|---|
| 3,144,445 | 8/1964 | Grant et al...................... | 260/239.1 |
| 3,157,640 | 11/1964 | Johnson et al.................. | 260/239.1 |
| 3,180,862 | 4/1965 | Silvestri et al................. | 260/239.1 |
| 3,299,046 | 1/1967 | Alburn et al.................... | 260/239.1 |

FOREIGN PATENTS OR APPLICATIONS

| | | | |
|---|---|---|---|
| 1,003,868 | 1965 | United Kingdom............ | 260/239.1 |
| 1,160,102 | 1969 | United Kingdom............ | 260/239.1 |

*Primary Examiner*—Gerald A. Schwartz
*Attorney, Agent, or Firm*—Bacon & Thomas

[57] ABSTRACT

A new anhydrous form of ampicillin is described. The new form is stable and relatively highly soluble, and may be prepared by heating ampicillin trihydrate rapidly to a temperature of above about 100°C, for example by contact with a hot water-immiscible liquid.

1 Claim, 4 Drawing Figures

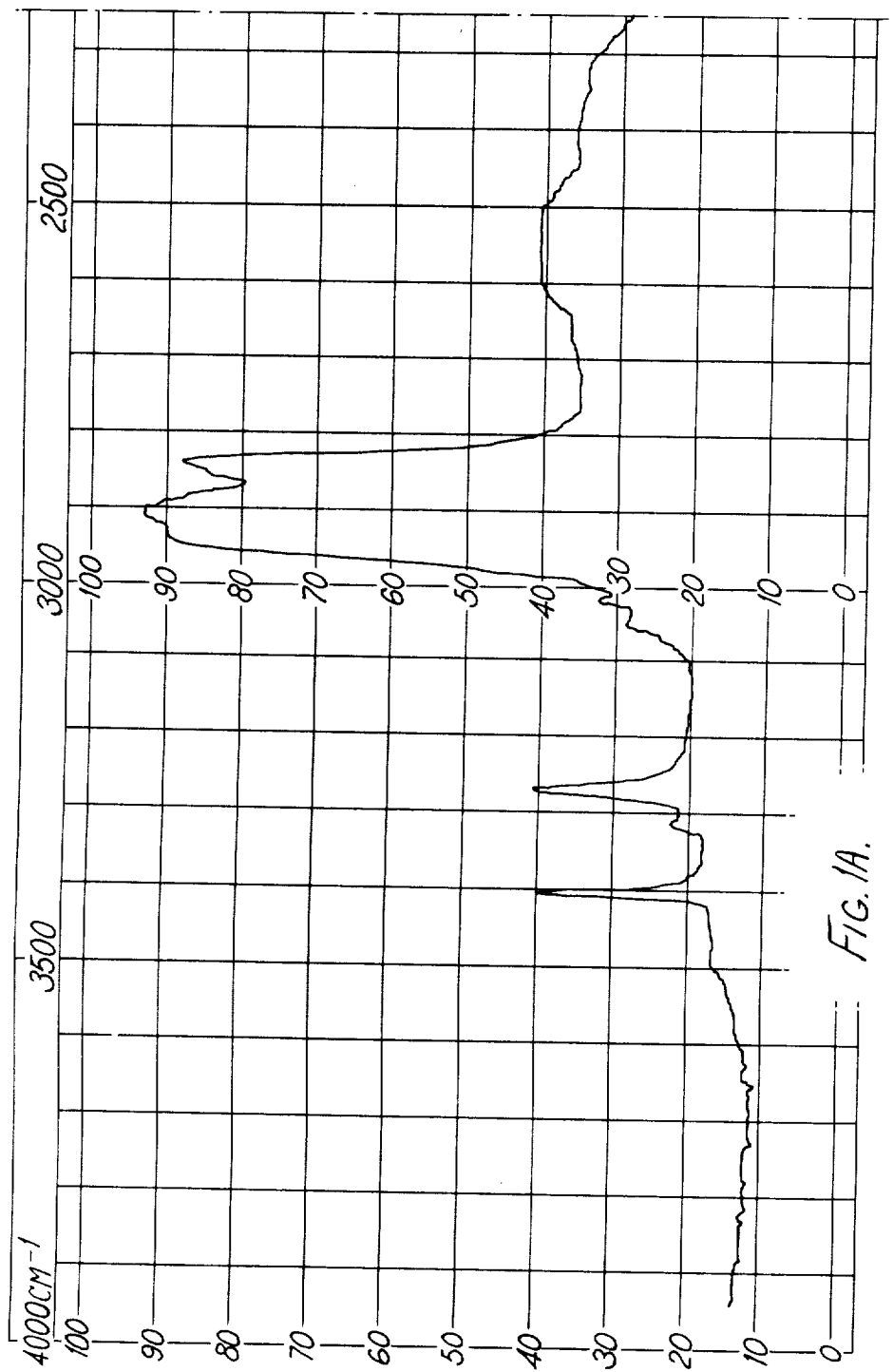

ANTIBIOTICS

This invention relates to penicillins and particularly to a new form of ampicillin, otherwise known as D-(−)-α-aminobenzylpenicillin, D-6-(2-amino-2-phenylacetamido) penicillanic acid, 6-[D-(−)-α-aminophenylacetamido] penicillanic acid, or 6β-(2-amino-2-phenylacetamido)-2, 2-dimethylpenam-3-carboxylic acid.

Ampicillin is a valuable antibacterial agent and is known to exist in several forms. An important form, commercially, is a hydrated form, the trihydrate hereinafter referred to in this specification as the α-form, but an anhydrous form has been described in British Patent Specification 1,003,868. The ampicillin anhydrate is referred to in that specification as ampicillin B and will be referred to herein as the γ-form of ampicillin.

A further form of ampicillin has been described in British Patent Specification 1160102. This form is stated in said specification to be an anhydrate, and although its precise nature is both uncertain and variable it is believed to be a mixture of two or more different forms of ampicillin.

We have now surprisingly found a novel and distinct anhydrous form of ampicillin, which will be referred to herein as the δ-form.

The new δ-form of ampicillin is a pure or substantially pure anhydrous form and has substantial and unexpected properties compared with previous described forms. Thus it has good stability characteristics in that it is only very slightly hygroscopic, and is also relatively highly soluble in water. The new form is for example more soluble in water at ambient temperature than either the γ-form referred to above or the α-form (i.e. ampicillin trihydrate).

The δ-form of ampicillin is characterised by its infrared spectrum, and by its X-ray characteristics. In its infrared spectrum there are two distinctive peaks at approximately 3287 and 3420 $cm^{-1}$. These two peaks are of medium strength, as determined on a Nujol mull of the δ-form of ampicillin using a Perkin-Elmer Model 521 Infrared Spectrophotometer using KBr plates for the mulls. The two peaks are sharp and separate, in that there is between them a region of minimal absorbance similar to the background level. The γ-form of ampicillin in contrast shows by the same method a single strong distinctive peak in this area of the spectrum (i.e. between about 3200 $cm^{-1}$ and 3450 $cm^{-1}$) at approximately 3335 $cm^{-1}$.

FIG. 1 (A&B) of the accompanying drawings shows the full infrared spectrum of the δ-form of ampicillin as obtained by the above method. A list of the frequencies at which peaks are observed is set out according to convention in the following Table:

Table I

| Infra-red peaks ($cm^{-1}$) of Nujol Mulls of δ-form Ampicillin | | | |
|---|---|---|---|
| 518 | w | 1236 | m |
| 528 | w.sh. | 1256 | m |
| 573 | vw | 1320 | m |
| 606 | vw | 1339 | s |
| 646 | vw | 1368 | m |
| 663 | vw | 1377 | m * |
| 699 | s | 1399 | s |
| 746 | m | 1458 | s * |
| 760 | m | 1518 | vs |
| 888 | vw | 1550 | s.sh |
| 924 | vw | 1705 | s |
| 975 | vw | 1766 | vs |
| 1006 | vw | 2600 | m |
| 1020 | w | 3287 | m |
| 1076 | w | 3420 | m |
| 1096 | m | | |
| 1127 | m | | |
| 1157 | m | | |
| 1194 | w | | |
| 1206 | vw | | |

Figure 2A:
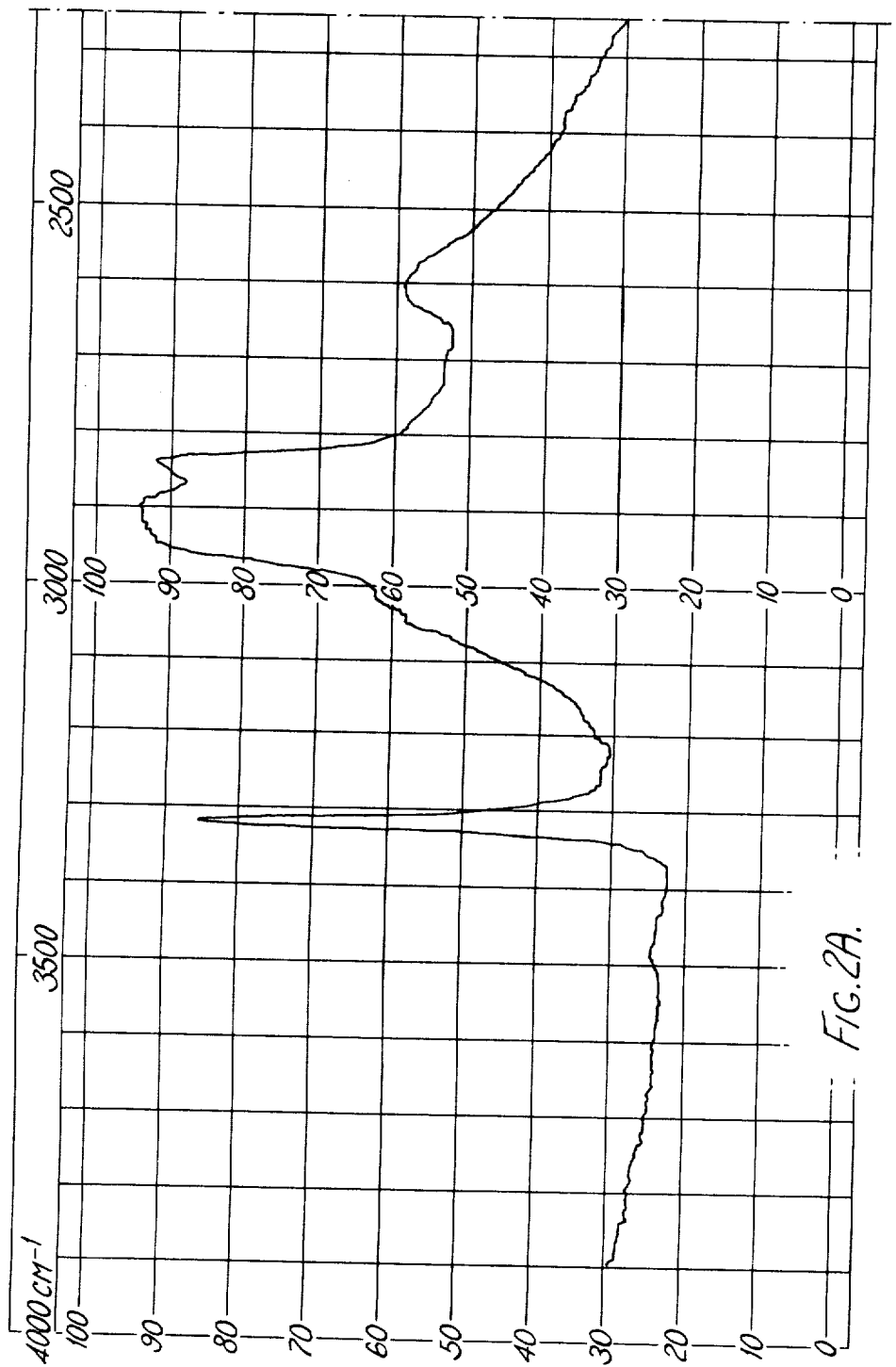
Figure 2B:
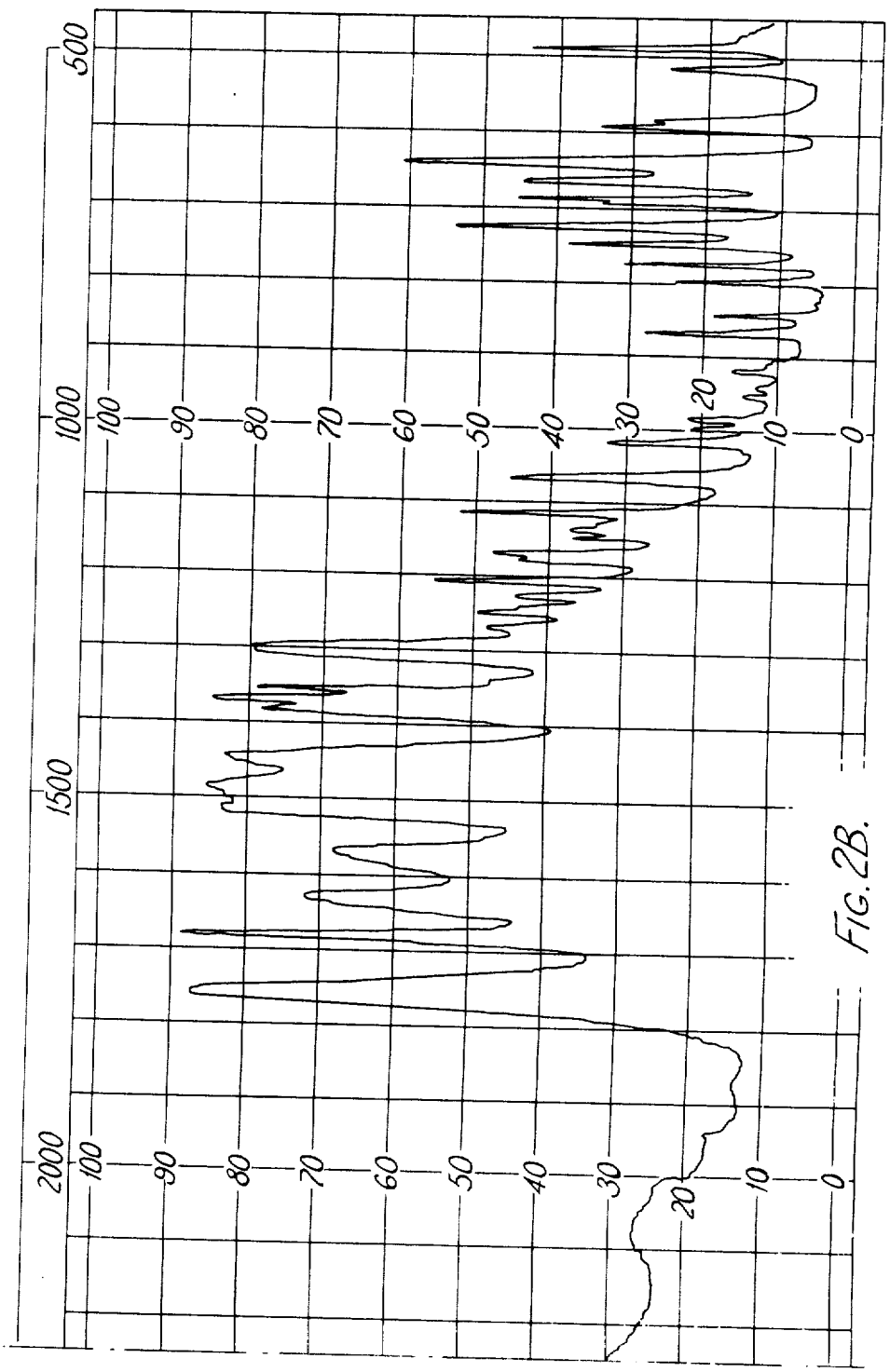

\* These peaks include absorption due to Nujol at 1376 and 1458.
s = strong
m = medium
w = weak
v = very  sh = shoulder For comparison, the infrared spectrum of the γ-form of ampicillin (obtained according to the above method) is shown in FIG. 2 (A&B) of the accompanying drawings; also a list of frequencies at which peaks appear is given in the following Table:

Table II

| Infra-red peaks ($cm^{-1}$) of Nujol Mulls of γ-form Ampicillin | | | |
|---|---|---|---|
| 493 | m | 1179 | m |
| 520 | w | 1187 | m |
| 587 | w | 1218 | m |
| 595 | w | 1236 | m |
| 645 | s | 1258 | m |
| 669 | m | 1278 | m |
| 692 | m | 1309 | vs |
| 730 | m | 1349 | m |
| 752 | m | 1365 | s |
| 778 | w | 1381 | vs * |
| 801 | vw | 1392 | vs |
| 846 | vw | 1458 | vs * |
| 873 | w | 1499 | vs |
| 991 | vw | 1525 | vs |
| 1006 | vw | 1582 | s |
| 1025 | w | 1640 | s |
| 1076 | m | 1692 | vs |
| 1125 | m | 1772 | vs |
| 1147 | m | 2625 | m |
| 1157 | m | 3335 | vs | s = strong
m = medium
w = weak
v = very
*These peaks include absorption due to Nujol at 1376 and 1458.

It will be seen that the characteristic peaks of the δ-form at 3287 $cm^{-1}$ and 3420 $cm^{-1}$ do not appear in the spectrum of the γ-form.

It will also be appreciated from a comparison of Tables I and II that the infra red spectrum of the δ-form has many characteristic features other than the two peaks appearing at 3287 $cm^{-1}$ and 3420 $cm^{-1}$. Thus for example the δ-form also shows certain characteristic features in the carbonyl region of the spectrum (about 1400 $cm^{-1}$ to 1800 $cm^{-1}$), particularly in that the peak at about 1640 $cm^{-1}$ present in the spectrum of the γ-form is absent in the spectrum of the δ-form, and the strong or very strong peaks shown at 1499, 1525 and 1582 $cm^{-1}$ in the spectrum of the γ-form are replaced in the spectrum of the δ-form by a very strong peak at 1518 $cm^{-1}$ having a shoulder at 1550 $cm^{-1}$. Again, the spectrum of the δ-form shows many distinct differences in the detailed "fingerprint" region of the spectrum from about 600 $cm^{-1}$ to 1200 $cm^{-1}$, particularly as regards the presence of sharp peaks at 699, 760, 888 and 1096 $cm^{-1}$. The latter peaks do not appear in the spectrum of the γ-form, which itself shows sharp peaks at for example 730, 801, and 846 $cm^{-1}$ which do not appear in the spectrum of the δ-form.

X-Ray powder photographs show that the δ-form of ampicillin exhibits characteristic d-spacings and intensities. X-Ray powder data for the δ-form is set out in Table III below. The photographs on which the data are based were taken with a Philips Debye-Scherrer camera (114.6 mm. diameter, Straumanis mounting) using copper Kα (nickel filtered) radiation, λ=1.5418A.

Table III

| X-Ray Powder Data of δ-form Ampicillin | | | |
|---|---|---|---|
| d(A) | I | d(A) | I |
| 13.76 | vvs | 3.35 | s |
| 10.88 | m | 3.21 | vw |
| 7.99 | w | 3.09 | m |
| 6.68 | s | 3.02 | vw |
| 6.05 | vw | 2.95 | w |
| 5.74 | vs | 2.84 | vw |
| 5.46 | vs | 2.74 | m |
| 5.23 | m | 2.70 | m |
| 4.82 | s | 2.60 | m |
| 4.59 | w | 2.52 | m |
| 4.51 | s | 2.42 | vvw |
| 4.39 | vw | 2.35 | vvw |
| 4.10 | m | 2.30 | w |
| 4.02 | vw | 2.18 | m |
| 3.62 | m | 2.13 | vvw |
| 3.50 | w | 1.99 | w |
|  |  | 1.92 | w | v = very
s = strong
m = medium
w = weak
I = intensity

Tables IV and V below list for comparative purposes the d-spacings and line intensities obtained by the same technique for the γ-form and ampicillin trihydrate (described by us as α-form of ampicillin). These date again illustrate the distinct nature of the δ-form.

Table IV

| X-Ray Powder Data of γ-form Ampicillin | | | |
|---|---|---|---|
| d(A) | I | d(A) | I |
| 11.16 | s | 3.12 | vw |
| 6.51 | vvw | 3.07 | w |
| 6.13 | vw | 2.98 | m |
| 5.96 | vw | 2.90 | w |
| 5.60 | w | 2.80 | w |
| 5.35 | vvs | 2.74 | w |
| 5.13 | vw | 2.65 | vw |
| 4.50 | vvw | 2.61 | w |
| 4.35 | m | 2.56 | vvw |
| 4.27 | w | 2.49 | vw |
| 4.09 | s | 2.43 | vvw |
| 3.94 | m | 2.38 | vvw |
| 3.86 | s | 2.29 | w |
| 3.74 | vvw | 2.25 | w |
| 3.62 | vvw | 2.18 | w |
| 3.53 | m | 2.11 | vw |
| 3.41 | w | 2.05 | vw |
| 3.34 | w | 2.02 | vvw |
| 3.23 | vvw | 1.95 | vw |

Table V

| X-Ray Powder Data for α-form Ampicillin | | | |
|---|---|---|---|
| d(A) | I | d(A) | I |
| 12.19 | w | 2.97 | vw |
| 7.80 | vvw | 2.91 | vw |
| 7.20 | s | 2.80 | m |
| 5.84 | vs | 2.73 | w |
| 5.45 | m | 2.69 | w |
| 5.11 | m | 2.57 | m |
| 4.88 | s | 2.51 | m |
| 4.54 | m | 2.39 | w |
| 4.43 | m | 2.26 | m |
| 4.24 | vvw | 2.20 | w |
| 4.07 | w | 2.14 | m |
| 3.99 | m | 2.10 | w |
| 3.83 | vw | 2.03 | m |
| 3.74 | s | 1.95 | m |
| 3.59 | vvw | 1.92 | vvw |

Table V-continued

| X-Ray Powder Data for α-form Ampicillin | | | |
|---|---|---|---|
| d(A) | I | d(A) | I |
| 3.46 | s | 1.87 | vvw |
| 3.29 | s | 1.84 | w |
| 3.23 | vvw | 1.80 | vw |
| 3.15 | vvw | 1.78 | vw |
| 3.06 | s |  |  |

In Tables IV and V the abbreviations have the same meaning as in Table III.

The δ-form of ampicillin can be regarded as an anhydrate in that it is crystallographically substantially free of water. It thus generally contains only up to about 2% by weight of water, and samples we have prepared were usually found to contain about 1%.

In tests we have carried out we have found it possible to prepare the δ-form in a high state of purity, i.e. containing not more than 3% by weight of other forms of ampicillin. For practical purposes the δ-form is thus substantially pure.

It will be appreciated from the above that the invention is concerned with the δ-form of ampicillin, and does not include within its scope mixtures or compositions containing both the δ-form and significant (i.e. more than about 10% by weight) amounts of other anhydrous forms of ampicillin, such as the γ-form referred to above. That is, insofar as the invention does include within its scope mixtures or compositions comprising the new δ-form, these should be free of significant amounts of other anhydrous forms of ampicillin. However the invention comprises δ-ampicillin in combination with material other than other forms of ampicillin, such as pharmaceutical carriers, excipients, medicaments other than ampicillin and the like.

As in the case of the other forms of ampicillin, the δ-form of the invention has useful antibacterial activity and is of particular interest on account of its stability and solubility characteristics hereinbefore referred to. The invention thus also includes pharmaceutical (including veterinary) compositions comprising the δ-form of ampicillin together with a pharmaceutical carrier or excipient. The invention further includes a method of treating bacterial infections comprising administering to a subject the δ-form of ampicillin as hereinbefore defined.

The δ-form of ampicillin of the invention may be formulated for administration by the same methods as for the other forms of ampicillin.

The new form of ampicillin may for example be prepared by rapidly heating ampicillin trihydrate to a temperature of above about 100°C, e.g. to above 110°C and preferably 120°C – 130°C or 140°C. The heat can conveniently be applied by contacting ampicillin trihydrate with a relatively large volume of a suitably hot liquid.

The volume of hot liquid to be used in relation to the amount of ampicillin trihydrate will depend on factors such as its thermal conductivity and temperature and the time it is left in contact with the trihydrate. Suitable amounts of liquid can be determined by routine preliminary experiment. We have in general found it convenient to use at least 10 mls, preferably about 50 mls, of the liquid per gram of ampicillin.

The liquid must of course be one which boils at or above the temperature to which it is desired to heat the ampicillin trihydrate, and chemically inert to ampicillin.

The liquid should be water immiscible; that is for example a liquid in which water is soluble in an amount of not more than about 0.03% w/v. It should of course be a liquid in which ampicillin is insoluble or only very slightly soluble or only dissolves slowly (in relation to the time the ampicillin is in contact with the liquid). We have found that many such liquids are suitable for this purpose, particularly liquid hydrocarbons (which expression includes substituted hydrocarbons, substituted for example by halogen atoms). It will be appreciated that the precise chemical nature of the liquid is immaterial provided that it is inert to ampicillin and water immiscible as referred to above. Examples of suitable liquids are decalin, n-decane, dec-1-ene, bromobenzene, m-dichlorobenzene, t-butylbenzene 1-bromohexane, bromocyclohexane, n-octane, and xylene. We prefer to use decalin as the liquid.

We have found that the liquids just mentioned may be used at any suitable temperature, and in some cases up to their boiling points, but as indicated above temperatures of 120°C – 130°C or 140°C are generally quite satisfactory.

The time for which the ampicillin trihydrate is kept in contact with the hot liquid need only be very short. With the liquids mentioned above we have found that a contact time of 5 seconds may be sufficient, although longer (e.g. up to 30 minutes) may be used. The contact time is of course desirably kept to a minimum to avoid damage to the β-lactam ring. The contact may be effected in any suitable manner. For example, we have found it convenient to place the trihydrate on a filter (e.g. a sintered funnel) and then to introduce the hot liquid onto the filter. The liquid can then merely be allowed to drain off through the filter or can be drawn through it (e.g. by vacuum) at the end of the contact period.

The new form of ampicillin may also be prepared by effecting the rapid heating of the α-form on its own in a sealed container, as for example in a differential scanning calorimeter at rates of for example 64°C/minute or above. As with the method described above, the necessary rate of heating required to produce the desired form can be readily determined by simple experiment.

As is commonly found in cases of polymorphism the preparation of the desired form can be adversely affected by the presence of trace quantities of impurities, and such impurities should if necessary be first removed. The trihydrate used in the production of the δ-form is thus preferably freshly prepared or regenerated, for example by reprecipitation or recrystallisation. This may for example be effected by dissolving ampicillin trihydrate in an acid (e.g. a mineral acid such as hydrochloric acid) or a base (e.g. an inorganic base such as sodium hydroxide or an organic base such as triethylamine) and thereafter adjusting the pH to about 5 to re-precipitate the trihydrate. Similarly, the trihydrate may be dissolved in acid and base then added to give an alkaline pH prior to adjusting the pH to 5 with acid.

While we do not wish to be limited by theoretical considerations, the experiments we have carried out in connection with the methods described above for the preparation of the new form of ampicillin have led us to believe that the new form is the thermodynamically stable anhydrate above a transition point of 105°± ca. 5°C. The practical conditions for obtaining the δ-form are not, we believe, dictated solely by thermodynamic considerations and thus for example we believe that it is necessary to heat the starting material sufficiently rapidly to avoid the formation of the γ-form of ampicillin which is not itself readily converted into the desired δ-form. Our experiments have also led us to believe that the transition from the α-form into the δ-form should take place in contact with water vapour at not less than the partial pressure that would be in equilibrium with the α-form at the temperature in question. Thus we believe the effect of heating the α-form in a water immiscible liquid or in a sealed container is to ensure that the ampicillin is heated in contact with water vapour; in the case of the liquids we believe that the water vapour is entrapped around the ampicillin. At the temperatures in question this equilibrium partial pressure in the reaction zone will not be more than the saturated steam pressure and at temperature of for example about 110°C it will probably not be significantly different from the saturated pressure; thus the conversion may conveniently be effected in contact with water vapour saturated at the temperature in question, i.e. at a partial pressure of at least 6 p.s.i. (gauge) and preferably at about 14 p.s.i. (gauge). It will therefore be appreciated that the method of the invention may be said to comprise heating the α-form of ampicillin to a temperature of above about 100°C in the presence of water vapour in a reaction zone saturated at that temperature whereby the new form of ampicillin is formed. Our experiments have also led us to believe that other heat transfer techniques may be used to provide conditions necessary for the formation of the δ-form, as for example by suspending the α-form in a finely divided state in a stream of hot gas saturated with water vapour, e.g. by using a fluidised bed of the α-form and a suitably hot stream of saturated steam, such as at 120°C and a water vapour pressure of 14 p.s.i. The gas stream may optionally be diluted with an inert gaseous diluent such as nitrogen.

The following examples illustrate the preparation of the δ-form of ampicillin.

EXAMPLE 1

Ampicillin trihydrate (5.0g) was dissolved in 0.1M HCl (50 ml). The pH was adjusted to pH 1 (conc. HCl), the solution filtered, the pH adjusted to pH 6.6 by addition of triethylamine and then back to 5.0 by addition of concentrated hydrochloric acid. After refrigeration for 30 minutes the mixture was filtered, washed with cold water and air dried at 35° for 16 hours, to give 3.9 g of regenerated ampicillin trihydrate ($[\alpha]_D$ + 255° c 0.282 $H_2O$).

Ampicillin prepared in this way (5 g) was placed in a 3 inch sintered-glass filter funnel. Decalin (250 ml) was heated to 120° and poured into the funnel. The mixture was stirred with a spatula for 10 seconds and the vacuum then applied. Filtration took 5 seconds. The product was washed with ethyl acetate and diethyl ether and dried at 55° under vacuum. Yield 4.3 g (99% theory) white powder (Colour measured in a Lovibond Tintometer using 10% w/v solution in 1.0 N ammonia in a 2 cm cell:0.2Y, 0.2R).

The i.r. spectrum of the product was identical to that shown in the accompanying drawing and showed that the product contained not less than 97% of the δ-form.

EXAMPLE 2

The preparation described in Example 1 was repeated with decalin and a number of other liquids at 140°C, using 0.5g of the regenerated trihydrate and 25 ml of the liquid at a contact time of 10 seconds. The results are summarized in the following Table.

Table VI

| Liquid | % δ-form produced |
|---|---|
| decalin | >97 |
| n-decane | >97 |
| dec-1-ene | >97 |
| 1-bromohexane | >97 |
| bromocyclohexane | >97 |
| n-octane | >97 (120°C) |
| xylene | 95 |

EXAMPLE 3

Example 1 was repeated using freshly prepared ampicillin trihydrate instead of the regenerated material. 6-Aminopenicillanic acid (21.6 g) in methylene chloride (225 ml), triethylamine (28 ml) and dimethylaniline (13.9 ml) were stirred for 15 minutes at room temperature and then cooled to 10°C. Dimethyldichlorosilane (12 ml) was added over 10 minutes (temperature 10°–15°), refluxed for 1 hour then cooled to 10°C and dimethylaniline 1.9 HCl (1.05 g in 5 ml $CH_2Cl_2$) was added. The mixture was cooled to 5°C and phenylglycylchloride hydrochloride (21.9 g 94% pure) was added in one portion and stirred at 5°C for 3½ hours. Cold water was added (250 ml) and stirred for 10 minutes then filtered through Clarcel F10 (diatomaceous filter-aid). The layers were separated and the pale yellow organic layer was washed with water (30 ml). The total aqueous layer was cooled at 10°C and methyl isobutyl ketone (50 ml) added. The pH was raised from 1 to 2.5 at 10°C with 10M NaOH (~ 3 ml) and stirred for 10 minutes when crystallisation occurred. The pH was then slowly brought to 5.1 over 30 minutes by dropwise addition of 10M NaOH. The mixture was kept at 4°C overnight and the product removed by filtration, washed with ice-cold water (100 ml), methyl isobutyl ketone (2 × 100 ml) and dried in an air oven at 37°C.

Yield of ampicillin trihydrate = 82%. The trihydrate was converted into δ-form ampicillin as in Example 1, and also gave a product containing not less than 97% δ-form.

EXAMPLE 4

Finely ground regenerated α-ampicillin (2.7 mg) was encapsulated in a hermetically sealed volatile sample pan (Perkin-Elmer).

The sample was run on a Perkin-Elmer differential scanning calorimeter, model DSC 1B, from a starting temperature of 330°K(57°C) to 410°K (137°C) at a scan speed of 64°/min. on range 8 and with a chart speed of 120 mm/min. An endothermic transition was observed at 383°K (110°C). After the run an infrared spectrum on the sample showed it to be > 97% δ-form ampicillin.

We claim:
1. An anhydrate of ampicillin having an infrared spectrum substantially as characterised in FIG. 1 of the accompanying drawings.

* * * * *